United States Patent [19]
Bouhour et al.

[11] Patent Number: 5,938,687
[45] Date of Patent: Aug. 17, 1999

[54] METHODS AND APPARATUS FOR PROCESSING TROUBLES OF THE ATRIAL RHYTHM

[75] Inventors: Anne Bouhour, Ville D'Avray; Marcel Limousin, Paris; Jean-Luc Bonnet, Montrouge, all of France

[73] Assignee: ELA Medical S.A., Montrouge, France

[21] Appl. No.: 09/102,447

[22] Filed: Jun. 22, 1998

[30] Foreign Application Priority Data

Jun. 20, 1997 [FR] France .................................. 97 07672

[51] Int. Cl.⁶ .................................................. A61N 1/362
[52] U.S. Cl. ............................................................ 607/15
[58] Field of Search ........................... 600/510; 607/14, 607/15, 9, 4, 5, 6

[56] References Cited

U.S. PATENT DOCUMENTS

| 5,226,415 | 7/1993 | Girodo et al. . |
| 5,271,394 | 12/1993 | Girodo et al. . |
| 5,312,451 | 5/1994 | Limousin et al. . |
| 5,318,594 | 6/1994 | Limousin et al. . |
| 5,403,356 | 4/1995 | Hill et al. . |
| 5,713,928 | 2/1998 | Bonnet et al. ............................ 607/9 |

FOREIGN PATENT DOCUMENTS

| 0 488 841 | 6/1992 | European Pat. Off. . |
| 0 488 904 | 6/1992 | European Pat. Off. . |

*Primary Examiner*—Scott M. Getzow
*Attorney, Agent, or Firm*—Orrick, Herrington & Sutcliffe, LLP

[57] ABSTRACT

A device and process for the processing of troubles of the atrial rhythm for an active implantable medical device. The device detects signals from at least the atrial cardiac activity, and stimulates both the atrial and ventricular cardiac cavities, detects the occurrence of atrial extra-systoles (ESA), and determines and releases an intermediate atrial escape interval (PPinter). The intermediate atrial escape interval is then applied during the detection of an atrial extra-systole for improved processing.

18 Claims, 3 Drawing Sheets

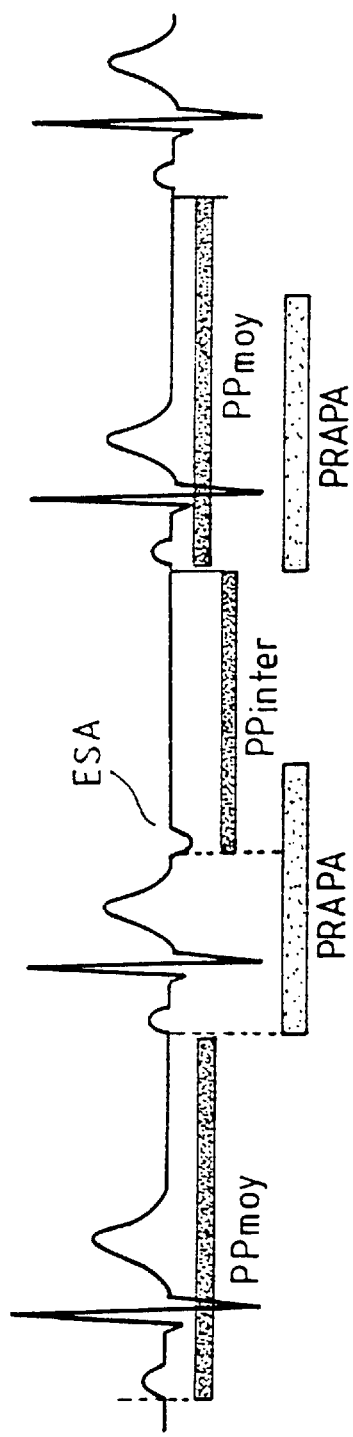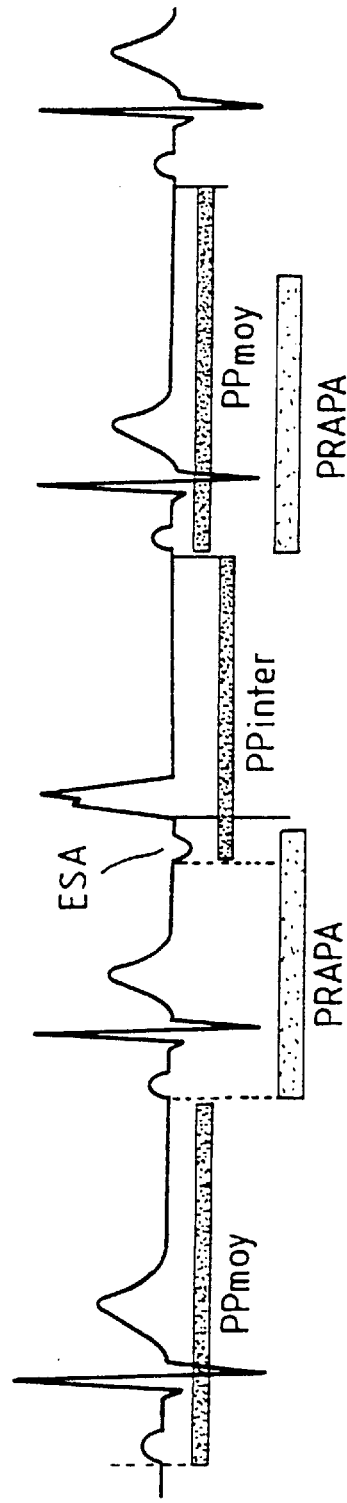

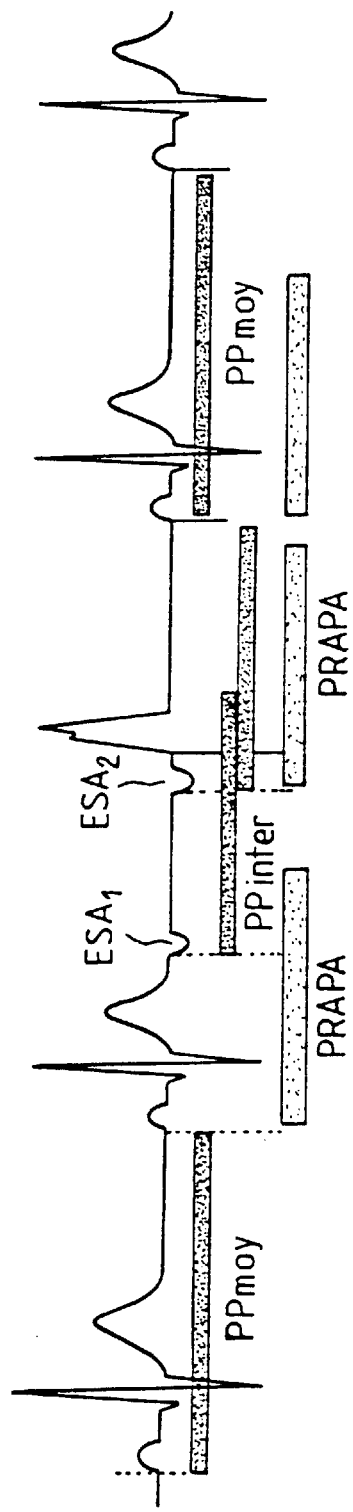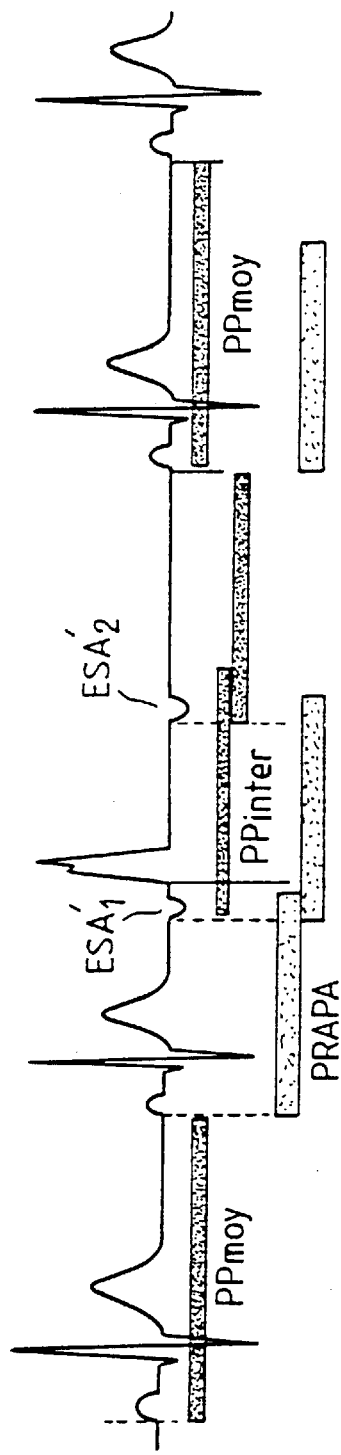
FIG_3
FIG_4

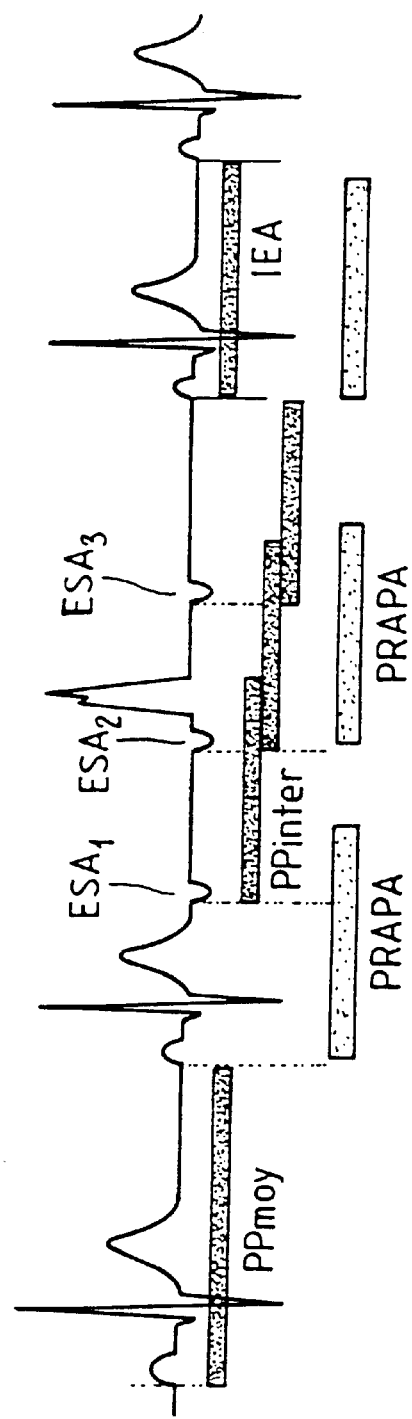
FIG_5
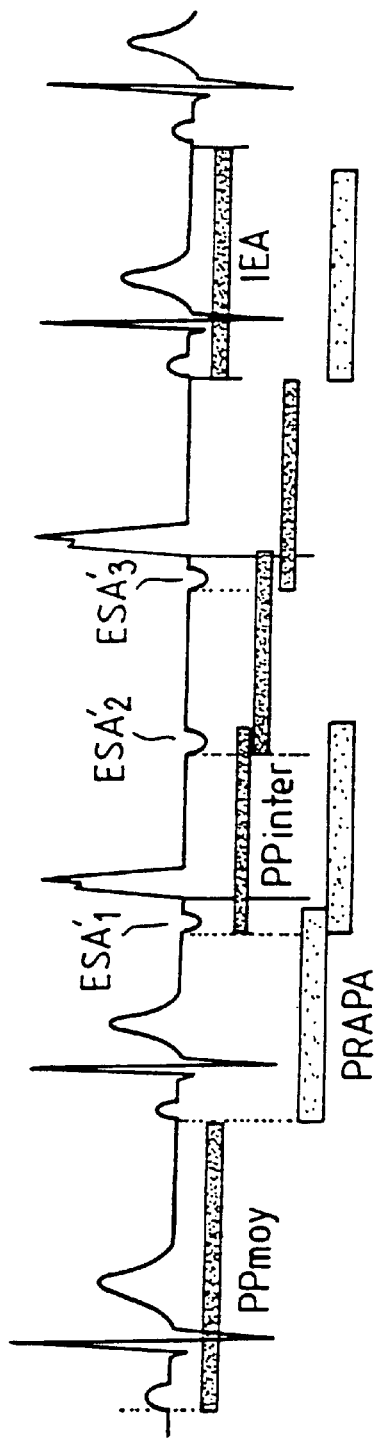
FIG_6

METHODS AND APPARATUS FOR PROCESSING TROUBLES OF THE ATRIAL RHYTHM

FIELD OF THE INVENTION

The present invention concerns an active implantable medical device, especially a device of the family including pacemakers, defibrillators and cardiovertors, having a double chamber stimulation function, for the processing of trouble of the atrial rhythm, as well as a process for the control of a such device. Such active implantable medical devices are defined, for example, in the Jun. 20, 1990 directive 90/385/EEC of the European Community Council.

BACKGROUND OF THE INVENTION

Among the known active implantable medical devices are "double" or "dual" chamber devices which collect (sense) and deliver (stimulate) signals in the high cavity (the atrium) and the low cavity (the ventricle) of the heart. These devices are designed to follow the cardiac rhythm of the patient and to undertake some diagnosis and/or therapy functions of an atrial arrhythmia (AA) and/or a ventricular arrhythmia (AV).

A process for the control of such a double chamber cardiac pacemaker in the case of a detection of a ventricular extrasystole (ESV) is described, for example, in EP-A-0 550 342, and its corresponding U.S. Pat. No. 5,312,451, which are commonly assigned and which disclosure is hereby incorporated herein by reference. This document describes a means for preventing trouble of the cardiac rhythm that can occur at the appearance of a ventricular extra-systole (ESV). A ventricular extra-systole can induce a pause, also known as a ventricular pause, that favours or can precipitate the establishment of a trouble of the cardiac rhythm by the desynchronisation of ventricular refractory periods. In these conditions, a tachycardia can be established.

It is not possible to anticipate the occurrence of a ventricular extra-systole. However, it is possible, according to the process described in EP-A-0 550 342 and U.S. Pat. No. 5,312,451, to warn of the dangerous consequences of such an event.

According to this known process, at the detection of a ventricular extra-systole, one stimulates the atrium simultaneously with the appearance of the ventricular extra-systole, and then one stimulates the atrium at a rhythm that is more rapid than the rhythm existing before the appearance of the ventricular extra-systole, decreases the atrio-ventricular (AV) delay during this rapid stimulation, and returns the stimulation rate slowly by steps to the base frequency existing before the appearance of the ventricular extra-systole. The ventricular pause is thus avoided. This technique has been successfully implemented with the help of programs downloaded into a memory of a microprocessor-based active implantable medical device, especially in the double chamber devices such as the CHORUS brand pacemakers manufactured by the assignee hereof ELA Medical.

Nevertheless, some limitations to the foregoing control process have been observed in clinical practice.

One of the disadvantages of the process mentioned above is that it processes only extra-systoles of ventricular origin, and does not attend to atrial extra-systoles (ESA) giving rise to the same phenomenon of desynchronisation, which also is prejudicial to a good stability of the cardiac rhythm.

Further, it has been observed during an occurrence of the so-called "doublets" or "triplets" of extra-systoles, that are, respectively, a sequence or "salvo" of two extra-systoles (ESA or ESV) or a continuation of three extra-systoles without an intermediary event of non extra-systolic origin, the process is deactivated and specifically does not processed this type of cardiac event.

In addition, it has been noted that the variation of the rhythm during a phase of acceleration after the detection of a ventricular extra-systole was not sufficiently physiological, because it does not take into account the precocity of the extra-systole.

Also, during the repeated appearance of a ventricular extra-systole during the activation of the algorithm of the process, the former has a tendency to accelerate the rhythm to an increasingly high frequency, and typically to the programmed maximal frequency. Such a successive acceleration, that is normally favourable, presents the problem that very often the frequency of stimulation does not correspond to physiological needs of the patient. For example, an acceleration increasing the frequency from 100 to 120 bpm is not problematical, but an acceleration from 50 bpm to a maximal frequency (typically at 120 bpm) is not appropriate if the patient is at rest.

OBJECTS AND SUMMARY OF THE INVENTION

It is, therefore, an object of the present invention to provide a device and a process for controlling a device to prevent troubles of the atrial rhythm which are susceptible to appear after the occurrence of one or more atrial extra-systoles, which takes into account not only an isolated atrial extra-systole, but also atrial extra-systoles appearing in the form of doublets or triplets (or salvos).

It is another object of the present invention to provide an improved adaptation to the acceleration of the cardiac rhythm after the detection of an atrial extra-systole (isolated or multiple) by taking into account the coupling of this extra-systole atrial with the atrial event preceding its appearance.

It is yet another object of the present invention to provide that the maximal frequency, to which the device tends to reach gradually in case of a re-activation of the algorithm, takes into account the average frequency of the previous sinusal rhythm. In the case of an enslaved device, the device can also take into account the average frequency indicated by the sensor of enslavement supplied with the device to evaluate the maximal acceleration frequency. It should be understood that an enslaved device is one that includes a sensor of enslavement which operates in a known manner to detect a physiological parameter (minute ventilation, pH, temperature, etc.) or a physical parameter of activity (acceleration) of the patient which is indicative of the patient's cardiac output requirements, such as are employed in the commercial CHORUM, CHORUS RM and OPUS G brand pacemakers, available from ELA Medical.

To this end, the present invention is directed to an improved active implantable medical device and a process having improved processing of troubles of the cardiac rhythm. One such active implantable medical device, according to the present invention, comprises means for detecting of signals in the atrial cardiac activity, means for producing cardiac stimulation in the atrium and the in ventricle of the heart, means for detecting the occurrence of atrial extra-systoles, and means for releasing (triggering) an intermediate atrial escape interval in response to a detected atrial extra-systole.

One such control process for an active implantable medical device, comprises:

a) detecting signals in the atrial cardiac activity, b) detecting the occurrence of atrial extra-systoles, and c) releasing an intermediate atrial escape interval and applying the intermediate atrial escape interval during the detection of an atrial extra-systole.

In a preferred embodiment, the device also comprises a means for decreasing the instantaneous escape interval (a mode of programmed acceleration) and, in an advantageous manner, the instantaneous escape interval is decreased in an iterative (stepwise) manner with each detection of a sequence of atrial extra-systoles until a predetermined maximal frequency, or a predetermined maximal frequency indicated by a sensor of enslavement, is reached.

According to an advantageous embodiment, if there is no programmed acceleration mode, the intermediate atrial escape interval is determined as a function of the coupling of the detected atrial extra-systole as compared to the preceding atrial event and the instantaneous escape interval that the device would have applied in the absence of the detected atrial extra-systole. For example, the intermediate atrial escape interval can correspond to an average between the interval of time separating the detected atrial extra-systole from the preceding atrial event, and the average interval of the atrial frequency.

If a phase of acceleration has been programmed at the appearance of the atrial extra-systole, the stimulation frequency is a function of the coupling of the extra-systole and the accelerated instantaneous escape interval calculated on the extra-systole.

According to another embodiment of the invention, the instantaneous escape interval corresponds to the average interval less a first percentage if the aforementioned average interval of the atrial frequency is less than a first interval of time, and to the average interval less a second percentage in the opposite case. Preferably, this interval of time is 600 ms, the first percentage is 12%, and the second percentage is 6%.

According to another embodiment, the invention includes a means for recycling the intermediate escape interval, which operates to recycle the intermediate escape interval if a new atrial extra-systole is detected during the released intermediate escape interval.

In one embodiment of the invention, the means for reducing the instantaneous escape interval (IE) preferably decreases it in an iterative manner at each sequence of detection of atrial extra-systoles (ESA) until reaching a maximal predetermined acceleration frequency (Fmacc). This maximal predetermined acceleration frequency can be conventionally programmed in advance, calculated, or otherwise determined in any appropriate manner. Preferably, the maximal acceleration frequency corresponds to the average frequency plus 30 bpm, if the average frequency is below 100 bpm, or the average frequency plus 20 bpm if the average frequency is above this 100 bpm threshold. Of course, one can use thresholds other than 100 bpm, as well as percentages other than 12% and 6% (which numbers also may vary to correspond to a microprocessor clock speed).

BRIEF DESCRIPTION OF THE DRAWINGS

Other features, characteristics, and advantages will appear to the person of ordinary skill in the art in view of the following detailed description of a preferred embodiment of the present invention, made with reference to the drawings annexed, in which:

FIG. 1 illustrates the functioning of a device according to the invention in the case of an early isolated atrial extra-systole without acceleration;

FIG. 2 illustrates the functioning of the device according to the invention in the case of a delayed isolated atrial extra-systole without acceleration;

FIG. 3 illustrates the functioning of the device according to the invention in the case of an early doublet of atrial extra-systoles without acceleration;

FIG. 4 illustrates the functioning of the device according to the invention in the case of a delayed doublet of atrial extra-systoles without acceleration;

FIG. 5 illustrates the functioning of the device according to the invention in the case of a triplet of early atrial extra-systoles with acceleration; and FIG. 6 illustrates the functioning of the device according to the invention in the case of a delayed triplet of atrial extra-systoles with acceleration.

DETAILED DESCRIPTION OF THE DRAWINGS

Referring to FIG. 1 shows the principle of a device functioning according to the invention in the case of an early isolated extra-systole atrial is shown.

A P-wave or a "P event" (namely, the sensing of spontaneous cardiac activity having its origin in the atrium) is defined as an atrial extra-systole ESA if the interval of time separating this wave from the preceding atrial event is less than a fraction of the average interval "PPmoy" of the calculated atrial frequency "Fmoy", for example, an interval corresponding to the frequency calculated over eight preceding cardiac cycles not having an extra-systole.

In the figures, the reference PRAPA designates a period of research of the post-atrial acceleration.

An atrial extra-systole is defined as a "delayed" extra-systole if the interval of time separating the atrial extra-systole from the preceding P wave is greater than 50% of the average interval PPmoy. If this interval is less than or equal to this rate, the atrial extra-systole is defined as an "early" extra-systole. If the atrial extra-systole is early (FIG. 1), one determines an intermediate escape interval "PPinter".

In a first preferred embodiment, the intermediate escape interval PPinter corresponds to the average of the coupling of the atrial extra-systole and the instantaneous escape interval IE calculated by the device in a known manner. The instantaneous escape interval IE is the average interval PPmoy in the case illustrated in FIG. 1 without acceleration being programmed. Preferably, the instantaneous accelerated escape interval "IEA" is equal to the average interval PPmoy less 12% (of this interval) if the average interval PPmoy is below 600 ms, and it is equal to PPmoy less 6% in the opposite case. Alternatively, one can relate in a different manner the coupling and PPmoy. In this manner, the atrial pause that would have been able to be established after the appearance of the atrial extra-systole is suppressed by the atrial stimulation (event A) that takes place at the end of the intermediate escape interval PPinter.

In the case of a delayed atrial extra-systole (FIG. 2), the means implemented as discussed for the early atrial extra-systole remain applied. In addition, one releases a atrio-ventricular delay "DAV", that is the delay between a P wave or an atrial stimulation event A and a following ventricular stimulation V, if the ventricular interval resulting from this DAV delay is greater than a programmable value, for example, of 400 ms. In the opposite case, one does not release the delay DAV.

Taking into account the coupling of the atrial extra-systole allows stabilization of the atrial rhythm in a more optimal manner. The introduction of a delay DAV in case of a delayed atrial extra-systole stabilises the ventricular rhythm and as a result one obtains, therefore, a smoothing of the cardiac rhythm and a better physiological adaptation.

In the case of atrial extra-systole doublets (FIGS. 3 and 4), the same distinction between delayed and early atrial extra-systoles is made.

FIG. 3 shows the case of the doublets of early atrial extra-systoles. The calculation of the intermediate escape interval PPinter follows the same rules discussed previously in the case of an isolated atrial extra-systole. For an atrial extra-systole $ESA_2$, the calculated interval PPinter released with the coupling of the first atrial extra-systole $ESA_1$ is recycled on the second atrial extra-systole $ESA_2$. It is applied only on the last atrial extra-systole of the salvo, in this case on the second atrial extra-systole $ESA_2$.

FIG. 4 illustrates an example of delayed doublets of extra-systoles. On the first atrial extra-systole $ESA_1$ of the salvo, it is seen as an isolated atrial extra-systole, and releasing of the atrio-ventricular delay DAV is managed as in the case of an isolated atrial extra-systole (as discussed above). On the detection of the next atrial extra-systole $ESA_2$ in the salvo, the intermediate escape interval PPinter is recycled. However, there is no new releasing of the delay DAV, resulting in a 2:1 Wenkebach function, and the device stimulates the atrium at the end of the delay interval PPinter.

The case of atrial extra-systoles triplets constitutes a generalisation of the case of the doublets, and is illustrated on FIGS. 5 and 6 with programming of a phase of acceleration. The two first atrial extra-systoles $ESA_1$ and $ESA_2$ are perceived by the device as a doublet and the delay interval PPinter is made effective on the last atrial extra-systole $ESA_3$.

In another preferred embodiment of the invention, illustrated for the case of triplets of atrial extra-systoles on FIGS. 5 and 6, on each isolated atrial extra-systole (a true isolated atrial extra-systole or a first atrial extra-systole of a salvo) which is a frequent extrasystole, the instantaneous escape interval IE, calculated by the device, is decreased by a first amount, e.g., a percentage of 12%, if the average interval PPmoy is below some value, e.g., 600 ms, and a second amount, e.g., a percentage less than the first amount of 6%, in the opposite case until the maximal acceleration frequency Fmacc (the accelerated escape interval IEA) is reached. In the absence of a frequent atrial extra-systole, the escape interval lengthens by following a programmed smoothing algorithm such that described in the European patent application EP-A-0 550 342.

The maximal acceleration frequency Fmacc is preferably evaluated as a function of the current rhythm. Preferably, it is equal to the frequency Fmoy corresponding to the average interval PPmoy plus 30 bpm if Fmoy is below 100 bpm, and Fmoy plus 20 bpm if Fmoy is above this threshold. One will refer advantageously to EP-A-0 488 841 and its corresponding U.S. Pat. No. 5,271,394, which is commonly assigned to ELA Medical, for a description of the calculation of the escape interval IE, which disclosure is hereby incorporated herein by reference.

Nevertheless, it is noted that when one has begun to accelerate on an atrial extra-systole, one no longer has the information on the current cardiac rhythm. The maximal acceleration frequency is then preferably controlled by the information delivered by the enslaved sensor in the device, according to this embodiment of the invention.

As long as frequent atrial extra-systoles occur, one keeps the calculated accelerated maximal frequency with the help of the average frequency Fmoy before the beginning of the acceleration, except that if the enslaved sensor indicates a recovery, or except that if the maximal acceleration frequency calculated according to the frequency obtained by the sensor Fmacc_capt rises above the maximal acceleration frequency Fmacc, the maximal acceleration frequency Fmacc_capt obtained by the sensor is evaluated and used in the same manner as the maximal acceleration frequency. In these last two cases, one will attribute to the maximal acceleration frequency Fmacc the value of the maximal acceleration frequency Fmacc_capt obtained by the sensor. Thus, one can have a maximal frequency Fmax that corresponds to the physiological or physical exercise state and real cardiac output needs of the patient.

As would be understood by a person of ordinary skill in the art, the foregoing may be implemented in an active implantable medical device by use of discrete circuits (analog and/or digital circuits) or, alternatively, by a microprocessor based device operating under software control, preferably the latter. Indeed, software suitable to perform the above described operations is believed to be easily written by and within the abilities of a person of ordinary skill in the art and may be stored in suitable memory, e.g., ROM, or in firmware.

In addition, because the foregoing need not require any additional circuits (other than the conventional circuits for acquiring cardiac event information and conditioning those signals for processing by a microprocessor, and circuits for delivering stimulation pulses typically already existing in the device), software for processing such cardiac data in accordance with the present invention may advantageously be loaded into a RAM or other memory of microprocessor based device for use, for example, after the device is implanted. Thus, software may be transferred by conventional telemetry into an already implanted device, and then programmed to operate or not operate as appropriate or as needed. Such conventional medical devices that might use the invention are known and include, for example, the CHORUS brand dual chamber cardiac pacemakers, which are available from ELA Medical S.A., Montrouge, France, the assignee hereof.

One skilled in the art will appreciate that the present invention can be practiced by other than the described embodiments, which are presented for purposes of illustration and not of limitation.

We claim:

1. An active implantable medical device, comprising:
    a) means for detecting a signal representative of atrial cardiac activity;
    b) means for stimulating cardiac activity in at least two cardiac cavities including an instantaneous escape interval;
    c) means for detecting an occurrence of an atrial extra-systole;
    d) means for determining an intermediate atrial escape interval as a function of the coupling of a detected atrial extra-systole as compared to a preceding atrial event and of the instantaneous escape interval that the device would have applied in the absence of said detected atrial extra-systole; and
    e) means for releasing and applying the intermediate atrial escape interval during the detection of an atrial extra-systole.

2. A device according to claim 1, further comprising:
    means for determining an average interval of the atrial cardiac activity;
    means for determining a first interval between a detected atrial extra-systole and a preceding atrial event;

wherein the intermediate atrial escape interval is an average of the first interval and the average interval of the atrial cardiac event.

3. A device according to claim 1, further comprising means for recycling the intermediate escape interval in response to a detected atrial extra-systole occurring during a released intermediate escape interval.

4. A device according to claim 1, further comprising means for decreasing to a predetermined maximal frequency the instantaneous escape interval in an iterative manner at each detection of a sequence of atrial extra-systoles.

5. A device according to claim 4, further comprising a sensor of enslavement having an output corresponding to a frequency related to a cardiac output requirement, wherein the means for decreasing the instantaneous escape interval operates to decrease the instantaneous escape interval to a maximal frequency corresponding to the sensor of enslavement output.

6. A device according to claim 4, further comprising means for determining an average atrial interval between atrial events not having a detected atrial extra-systole, and means for providing the instantaneous escape interval as a function of one of the average atrial interval less a first percentage if the average atrial interval is less than a predetermined time interval, and the average atrial interval less a second percentage if the average atrial interval is greater than the predetermined time period.

7. A device according to claim 6 wherein the first percentage is 12%, the second percentage is 6%, and the predetermined time interval is 600 ms.

8. A device according to claim 5, further comprising means for determining an average atrial interval between atrial events not having a detected atrial extra-systole, and means for providing the instantaneous escape interval as a function of one of the average atrial interval less a first percentage if the average atrial interval is less than a predetermined time interval, and the average atrial interval less a second percentage if the average atrial interval is greater than the predetermined time period.

9. A device according to claim 8 wherein the first percentage is 12%, the second percentage is 6%, and the predetermined time interval is 600 ms.

10. A device according to claim 5, further comprising means for determining an average atrial frequency of successive atrial events not having an intervening detected atrial extrasystole, wherein the predetermined maximal frequency is one of an average atrial frequency plus a first increment for said average atrial frequency being below a threshold value and the average atrial frequency plus a second increment for said average atrial frequency being above the threshold value.

11. A device according to claim 10 wherein the threshold value is 100 bpm, the first increment is 30 bpm and the second increment is 20 bpm.

12. A process of controlling of an active implantable medical device comprising:

a) detecting a signal corresponding to atrial cardiac activity;

b) detecting an occurrence of an atrial extra-systole;

c) providing an intermediate atrial escape interval as a function of a coupling between a detected atrial extra-systole and a preceding atrial event and an instantaneous escape interval the device would have applied in the absence of the detected atrial extrasystole; and d) applying the intermediate atrial escape interval during and in response to a detected atrial extra-systole.

13. The process according to claim 12, further comprising:

determining an average interval of the atrial cardiac activity;

determining a first interval between a detected atrial extra-systole and a preceding atrial event; and calculating the intermediate atrial escape interval as an average of the first interval and the average interval of the atrial cardiac event.

14. The process according to claim 12, further comprising recycling the intermediate escape interval in response to a detected atrial extra-systole occurring during a released intermediate escape interval.

15. A process according to claim 12, further comprising decreasing to a predetermined maximal frequency the instantaneous escape interval in an iterative manner at each detection of a sequence of atrial extra-systoles.

16. A process according to claim 15, wherein said device includes a sensor of enslavement having an output corresponding to a frequency related to a cardiac output requirement, wherein decreasing the instantaneous escape interval further comprises decreasing the instantaneous escape interval to a maximal frequency corresponding to the sensor of enslavement output.

17. A process according to claim 15, further comprising determining an average atrial interval between atrial events not having a detected atrial extra-systole, and calculating the instantaneous escape interval as a function of one of the average atrial interval less a first percentage if the average atrial interval is less than a predetermined time interval, and the average atrial interval less a second percentage if the average atrial interval is greater than the predetermined time period.

18. A process according to claim 16, further comprising determining an average atrial frequency of successive atrial events not having an intervening detected atrial extrasystole, comparing said average atrial frequency to a threshold frequency, and a first increment the predetermined maximal frequency to be one of an average atrial frequency plus a first increment for said average atrial frequency being below a threshold value and the average atrial frequency plus a second increment for said average atrial frequency being above the threshold frequency.

* * * * *

UNITED STATES PATENT AND TRADEMARK OFFICE
CERTIFICATE OF CORRECTION

PATENT NO. : 5,938,687
DATED : August 17, 1999
INVENTOR(S) : Bouhour et al.

It is certified that error appears in the above-identified patent and that said Letters Patent is hereby corrected as shown below:

Column 1, line 12, after "control of" delete "a" and after "such" insert --a--;

Column 2, line 2, after "non" insert -- -- --;

Column 2, line 29, before "after" delete "appear" and insert -- appearing --;

Column 2, line 41, after "of a" delete "re-activation" and insert -- reactivation --;

Column 2, line 61, after "atrium and" delete "the in" and insert -- in the --;

Column 2, line 67, after "device" delete ",";

Column 4, Lines 19-21, before "FIG. 1" delete "Referring to" and after "atrial" delete "is shown";

Column 4, lines 57-58, after "releases" delete "a" and insert -- an --; and after "that is" insert --, --;

Column 5, Line 37, after "frequent" delete "extrasystole" and insert -- extra-systole --;

Column 5, line 46, after "such" insert -- as --;

Column 6, line 31, after "memory" delete "of" and insert --or --;

Column 7, line 23, after "atrial" delete "interval" and insert-- intervals--;

UNITED STATES PATENT AND TRADEMARK OFFICE
CERTIFICATE OF CORRECTION

PATENT NO. : 5,938,687
DATED : August 17, 1999
INVENTOR(S) : Bouhour et al.

It is certified that error appears in the above-identified patent and that said Letters Patent is hereby corrected as shown below:

Column 7, line 35, after "atrial" delete "interval" and insert --intervals--;

Columns 7, lines 45-46, after "atrial" delete "extra systole" and insert --extra-systole --;

Column 7, line 55, after "controlling" delete "of";

Column 8, line 8, after "atrial" delete "extrasystole" and insert -- extra-systole --;

Column 8 line 46, after "atrial" delete "extrasystole" and insert -- extra-systole --;

Title page: delete "," after "Sutcliffe" in right column.

British spelling to American spelling

Column 1, line 34, after "that" delete "favours" and insert -- favors --

Column 1, line 36, before "of" delete "desynchronisation" and insert -- desynchronization --;

UNITED STATES PATENT AND TRADEMARK OFFICE
CERTIFICATE OF CORRECTION

PATENT NO. : 5,938,687
DATED : August 17, 1999
INVENTOR(S) : Bouhour et al.

It is certified that error appears in the above-identified patent and that said Letters Patent is hereby corrected as shown below:

Column 1, line 63, after "of" delete "desynchronisation" and insert -- desynchronization --;

Column 2, line 15, after "normally" delete "favourable" and insert -- favorable --;

Column 5, line 1, after "extra-systole" delete "stabilises" and insert --stabilizes --;

Column 5, line 27, before "of the case" delete "generalisation" and insert -- generalization --;

Signed and Sealed this

Twenty-fourth Day of April, 2001

NICHOLAS P. GODICI

*Attest:*

*Attesting Officer*   *Acting Director of the United States Patent and Trademark Office*